United States Patent [19]

van Andel

[11] Patent Number: Plant 6,036

[45] Date of Patent: Oct. 13, 1987

[54] ALSTROEMERIA NAMED STALIS

[75] Inventor: Jacob van Andel, Aalsmeer, Netherlands

[73] Assignee: Van Staaveren B.V., Aalsmeer, Netherlands

[21] Appl. No.: 805,750

[22] Filed: Dec. 6, 1985

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Charles W. Rummler; John B. Lungmus

[57] ABSTRACT

A new Alstroemeria cultivar characterized in particular by its profuse year around production of very large flowers, the lower petals of which are distinguished by a combination of Spinel Red body portions with the outer petal portions being of a lighter Neyron Rose color which contrasts with the smaller upper petals, the larger of which are generally of a Rhodonite Red coloration with the central body portion of a bright Naples Yellow color, the upper petals being strongly marked by short, Brown pencil stripes which extend lengthwise of the petals from near the base to the petal tips, the smaller one of the upper petals has no Yellow and has only a few Brown pencil stripes mainly at the outer end of the petal; this plant is also distinguished by its medium height and its strong, upright and vigorous growth habit with abundant foliage.

1 Drawing Figure

BACKGROUND OF THE NEW PLANT

This new Alstroemeria plant originated as a seedling resulting from my crossing of selected plants which are individually identified members of my breeding stock maintained at Aalsmeer, The Netherlands, for developmental purposes. This particular seedling was selected by me for propagation because of the very large size of its blooms, the delicate Red and Pink coloration of its large lower petals, and the contrasting Yellow and darker Red coloration of the upper petals. Asexual reproduction of this seedling was done by me and under my direction at Aalsmeer, The Netherlands, by root division through several generations, which demonstrated conclusively that the distinctive characteristics of the parent seedling would hold true from generation to generation and appeared to be firmly fixed. Propagation of this new Alstroemeria variety is now being carried on at Aalsmeer, The Netherlands, by dividing root stock.

DESCRIPTION OF THE DRAWING

This new variety of Alstroemeria plant is illustrated by the accompanying photograhic drawing which, in full

DESCRIPTION OF THE NEW PLANT

The following is a detailed description of my new Alstroemeria plant with color designations according to The R.H.S. Colour Chart of The Royal Horticulatural Society of London, England.

THE PLANT

Origin: Seedling.

Parentage:

*Seed parent.*—Stock Plant No. 8237-1 (unpatented).

*Pollen parent.*—Stock Plant No. 9186-1 (unpatented).

Classification:

*Botanic.*—Alstroemeria Hybrid.

*Commercial.*—Alstroemeria.

Form: Erect bush.

Height: Medium; about 130 cm.

Main Stem:

*Length.*—About 130 cm.

Growth: Upright, strong and vigorous.

Root Stock: Tuberous.

Foliage:

*Quantity.*—Abundant.

*Number of Leaves.*—Various, depending upon season.

*Size of leaf.*—Various, depending upon season.

*Leaf shape.*—Elliptic, with entire margins.
*Texture.*—Leathery.
*Color.*—Upper side — Middle Green.

THE BUD

Form: Pear shaped.
Size: Medium.
*Diameter.*—About 25 mm.
*Length.*—About 45 mm.
Calyx: This flower has no calyx and the six flower petals are a perianth.

THE FLOWER

Blooming habit: Profuse and continuous the year around.
Flower size: Very large.
*Diameter.*—About 55 mm.
*Depth.*—From 55 to 65 mm.
Borne: Singly.
Shape: Cup-shaped when bloom first opens and becoming funnel-like with petals curling outwardly when bloom matures.
Petalage:
*Number of petals.*—Six.
*Arrangement.*—Two concentric circles of three petals each.
*Form.*—Broad, obovate.
*Texture.*—Leathery.
*Appearance.*—Shiny.
*Color.*—Lower petals — 54B in the central body portion with lighter Neyron Rose Pink in the outer portions of the petals. Uppermost petals — Generally of a Rhodonite Red color but with a Naples Yellow central portion of each petal and each petal being covered with short, Brown pencil stripes which extend in the longitudinal direction from the petal base to the petal tip.
Persistence: The flowers hang on and dry.
Peduncle:
*Length.*—About 20 mm.
*Color.*—Light Green.
Lasting quality:
*On the plant.*—About 15 days.
*As a cut flower.*—About *10 days.*

REPRODUCTIVE ORGANS

Stamens:
*Number.*—Six.
*Arrangement.*—One opposite each petal.
Anthers:
*Color.*—Yellow.
Filaments:
*Color.*—Purple/Pink.
Pistils:
*Number.*—One.
*Color.*—Purple/Pink.
Stigma:
*Color.*—Purple/Red.

THE FRUIT

Fertility: The fruit is fertile.
Shape: Capsular.
Color at Maturity: Light Brown.

This plant is particularly noted for its profuse year around production of very large flowers of Red and Pink coloration and by its upright, vigorous and strong growth habit of medium height, and its abundant production of foliage.

I claim:

1. A new and distinctive Alstroemeria cultivar, substantially as herein shown and described, characterized by its continuous production of very large flowers having an unusual Pink and Red coloration and by its strong, upright growth habit with the flowers appearing in an umbel at the top of a stem of about 160 cm. in height.

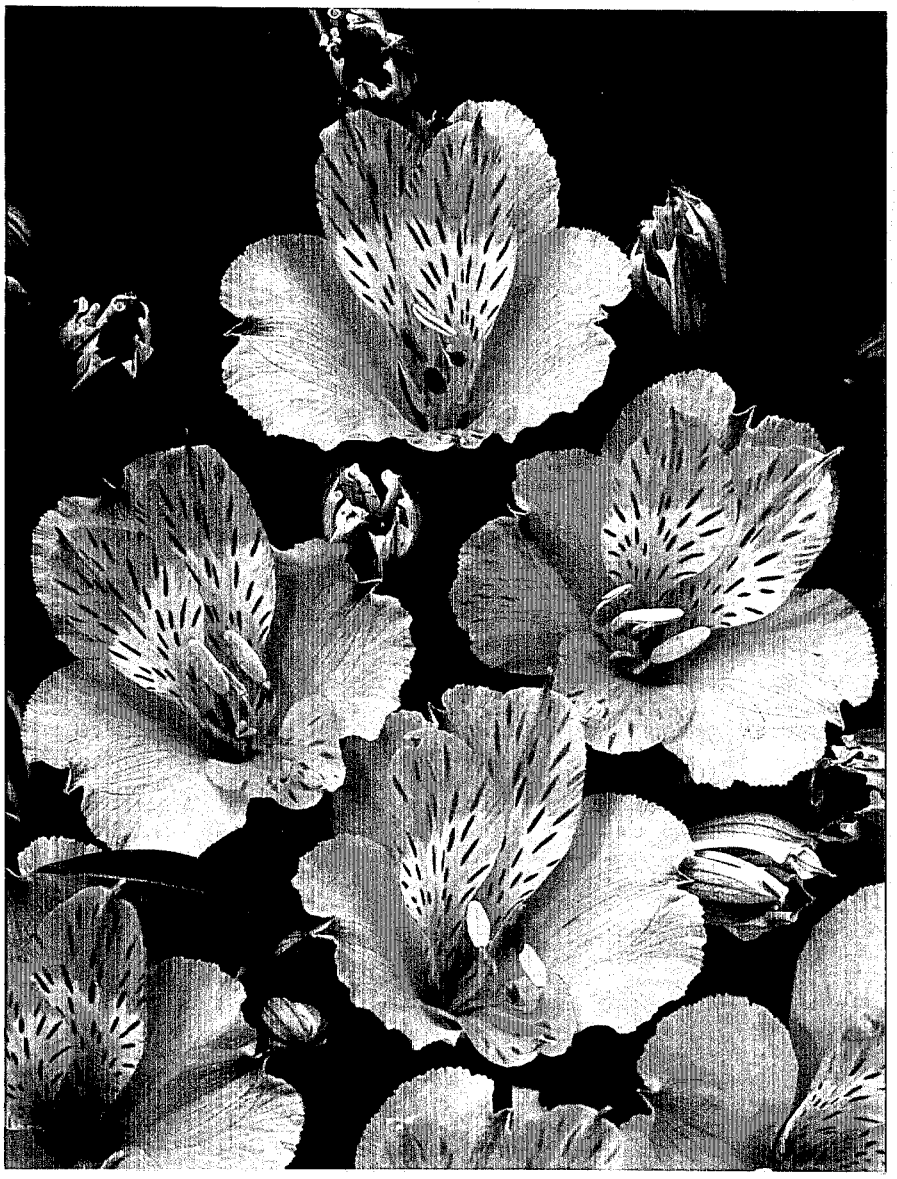

* * * * *